(12) United States Patent
Fukuda et al.

(10) Patent No.: US 7,147,905 B2
(45) Date of Patent: Dec. 12, 2006

(54) LAYERED PRODUCT AND MEDICAL SUPPLY COMPRISING THE LAYERED PRODUCT

(75) Inventors: Motohiro Fukuda, Tsukuba (JP); Naoto Fukuhara, Tsukuba (JP); Yukihiro Fujieda, Kurashiki (JP); Toshihide Nakashima, Kurashiki (JP); Koji Inai, Kurashiki (JP); Toshiji Ichikawa, Ono-gun (JP); Akira Ishida, Ono-gun (JP)

(73) Assignees: Kuraray Co., Ltd., Kurashiki (JP); Kawasumi Laboratories, Inc., Tokyo (JP)

( * ) Notice: Subject to any disclaimer, the term of this patent is extended or adjusted under 35 U.S.C. 154(b) by 229 days.

(21) Appl. No.: 10/491,901

(22) PCT Filed: Oct. 16, 2002

(86) PCT No.: PCT/JP02/10725

§ 371 (c)(1),
(2), (4) Date: Apr. 16, 2004

(87) PCT Pub. No.: WO03/033254

PCT Pub. Date: Apr. 24, 2003

(65) Prior Publication Data

US 2004/0241478 A1    Dec. 2, 2004

(30) Foreign Application Priority Data

Oct. 19, 2001   (JP) .............................. 2001-322777

(51) Int. Cl.
*B32B 1/08* (2006.01)
*B32B 27/08* (2006.01)
(52) U.S. Cl. .................... 428/36.91; 428/517; 428/521

(58) Field of Classification Search ................ 428/517, 428/521, 36.91
See application file for complete search history.

(56) References Cited

U.S. PATENT DOCUMENTS

| 4,133,731 A | 1/1979 | Hansen et al. ............... 522/110 |
| 4,151,057 A | 4/1979 | St. Clair et al. ............ 522/110 |
| 4,152,231 A | 5/1979 | St. Clair et al. ............ 522/110 |
| 4,311,759 A | 1/1982 | Glennon ..................... 428/345 |
| 4,432,848 A | 2/1984 | Korpman ..................... 524/533 |
| 4,447,488 A | 5/1984 | Simm et al. ................. 428/213 |

(Continued)

FOREIGN PATENT DOCUMENTS

| EP | 0 518 444 A1 * | 12/1992 |
| JP | 59-59761 | 4/1984 |
| JP | 1-188337 | 7/1989 |
| JP | 5-220908 | 8/1993 |
| JP | 5-230228 | 9/1993 |

(Continued)

*Primary Examiner*—D. S. Nakarani
(74) *Attorney, Agent, or Firm*—Oblon, Spivak, McClelland, Maier & Neustadt, P.C.

(57) ABSTRACT

A laminate comprising at least a surface layer (I) and an adjacent layer (II) thereto, characterized in that the surface layer (I) comprises a cross-linked copolymer formed by cross-linking a copolymer prepared by using as monomers at least one vinyl aromatic compound and at least one conjugated diene compound, and the adjacent layer (II) comprises a hydrogenated copolymer formed by hydrogenating a copolymer prepared by using as monomers at least one vinyl aromatic compound and at least one conjugated diene compound; a multilayer tube comprising the laminate; and a medical device comprising the laminate, and/or the multilayer tube.

12 Claims, 2 Drawing Sheets

U.S. PATENT DOCUMENTS

| | | | |
|---|---|---|---|
| 4,556,464 A | | 12/1985 | St. Clair .................... 524/274 |
| 4,716,183 A | * | 12/1987 | Gamarra et al. .............. 522/80 |
| 5,562,961 A | * | 10/1996 | Buchholz et al. .......... 428/36.5 |
| 6,517,949 B1 | * | 2/2003 | Mutsuda ..................... 428/501 |

FOREIGN PATENT DOCUMENTS

| | | |
|---|---|---|
| JP | 7-252397 | 10/1995 |
| JP | 2002-80688 | 3/2002 |

* cited by examiner

LAYERED PRODUCT AND MEDICAL SUPPLY COMPRISING THE LAYERED PRODUCT

TECHNICAL FIELD

The present invention relates to a laminate comprising at least a surface layer (I) and an adjacent layer (II) thereto, wherein the surface layer (I) and the adjacent layer (II) each comprises a specified copolymer, and a medical device comprising the laminate.

BACKGROUND ART

Japanese Patent Laid-Open No. Sho 59-59761 (Literature 1), U.S. Pat. No. 4,133,731 (Literature 2), U.S. Pat. No. 4,151,057 (Literature 3), U.S. Pat. No. 4,311,759 (Literature 4), U.S. Pat. No. 4,432,848 (Literature 5), and U.S. Pat. No. 4,556,464 (Literature 6) each discloses an adhesive composition prepared by cross-linking a composition comprising a block copolymer comprising a vinyl aromatic copolymer block and a conjugated diene polymer block, a tackifying resin and an acrylate ester with irradiation of radioactive rays. U.S. Pat. No. 4,152,231 (Literature 7) discloses a composition prepared by cross-linking a composition comprising a conjugated diene polymer, a tackifying resin and an acrylate ester with irradiation of radioactive rays.

Japanese Patent Laid-Open No. Hei 5-230228 (Literature 8) discloses a method for preparing a composition by irradiating a composition comprising a block copolymer comprising a poly(vinyl aromatic compound) block and a poly(conjugated diene) block, a thermoplastic polymer and a non-aromatic oil with an electron beam, and a shoe sole made of the composition.

Japanese Patent Laid-Open No. Hei 7-252397 (Literature 9) discloses a composition prepared by cross-linking a composition comprising a styrene-diene block copolymer, a hydrocarbon oil, a polyfunctional coupling agent and a light initiator with irradiation of an electron beam or ultraviolet rays.

Japanese Patent Laid-Open No. Hei 5-220908 (Literature 10) discloses a multilayer tube comprising at least one layer made of a polyamide or a polyester polymer, and another layer made of a polyolefin polymer, wherein the latter layer is cross-linked so as to give a gel fraction of 50% or higher.

U.S. Pat. No. 4,447,488 (Literature 11) discloses a sheet made of a synthetic resin or a natural rubber containing an additive other than a filler and a vulcanization accelerator, wherein the resin or the rubber comprises 3 to 95% by weight of at least one polymer component capable of being welded by heat and/or swelling agents, and capable of being cross-linked by high-energy irradiation.

Meanwhile, a tube pump is used as a means for quantitatively pumping a solution with a tube in an experiment such as liquid chromatography, and a medical practice using a blood circuit, an infusion tube or the like in artificial kidney dialysis. In the experiment such as liquid chromatography, currently, tubes made of silicone, polyethylene, ethylene tetrafluoride and vinyl chloride have been used. Tubes made of vinyl chloride have been used in a blood circuit, and tubes made of vinyl chloride, polyethylene, polybutadiene or the like have been used as an infusion tube.

DISCLOSURE OF INVENTION

Tubes and hoses, which are used for industries, foods or medicines, are required to have abrasion resistance of inner and outer surfaces because a load due to pumped contents, mechanical friction or the like is applied to the tubes and hoses. Especially, in a tube pump or the like, a solution is pumped by strongly squeezing a tube with a roller, so that tubes to be used are required to have abrasion resistance of inner and outer surfaces, especially, abrasion resistance of inner surface. When the abrasion resistance of inner and outer surfaces of tube is insufficient, a tube is scraped, so that substances detached from the inner surface is admixed into the solution. In addition, the observation of the contents may become difficult in some cases due to generation of scratches.

It is known that a flexible composition including a rubber or an elastomer is cross-linked, to give the composition abrasion resistance. In such a case, flexibility is generally sacrificed. However, it is not preferable to sacrifice the flexibility of the tube in order to obtain abrasion resistance. Tubes and hoses are in many cases used with bending utilizing their flexibility. Especially, a tube pump or the like is an apparatus to which a tube is attached with bending, and the attachment becomes difficult when the flexibility is insufficient. In addition, a decreased amount of the solution to be pumped and liquid leakage due to cracking of the tube may be generated, even if the tubes could be attached. The tubes currently used in a tube pump include those made of silicone, polyethylene, ethylene tetrafluoride, polybutadiene and the like. Those tubes are flexible, but do not necessarily have sufficient abrasion resistance.

In each of the compositions described in Literatures 1 to 4 and Literatures 6 to 9 and the molded articles obtained from the compositions, since the composition or the molded article is entirely cross-linked, the flexibility would be sacrificed. In the multilayer tube described in Literature 10, since one layer is a polyamide or a polyester polymer, its flexibility is insufficient. In addition, in the sheet described in Literature 11, only one side of the sheet is partially cross-linked by high-energy irradiation. Although it is necessary to complete cross-linking in order to obtain sufficient abrasion resistance, if energy is increased for this purpose, a cross-linked portion is increased, and flexibility is lowered. In order to obtain a flexible layer, it is necessary to make the sheet thicker, thereby making it difficult to control cross-linking degree (abrasion resistance), flexibility and thickness of the sheet.

As described above, it is desired that tubes and hoses for industrial, foods and medical uses satisfy both of abrasion resistance and flexibility, which have been generally very difficult to be achieved.

In addition, the transport state of the contents can be observed if contents of the tube can be seen. For instance, since the admixture of gas, foreign substances or the like into the tube can be confirmed, it is desired that the tube is transparent. In the compositions described in Literatures 1 to 8, other components such as a tackifying resin and an acrylate ester are formulated into the block copolymer comprising a vinyl aromatic copolymer block and a conjugated diene polymer block, so that their transparency becomes insufficient. In the multilayer tube described in Literature 10, one layer is made of a polyamide or polyester polymer, so that its transparency is insufficient.

On the other hand, a flexible material generally has high adhesion, so that when a dust, a foreign substance or the like attaches thereto, it cannot be simply removed. In the tubes and hoses for industrial, foods and medical uses as well as the medical devices, it is desired to have antifouling property since admixture of dusts or foreign substances is avoided as much as possible.

In addition, in the tubes and hoses for industrial or foods uses, vapor steam of around 120° C. may be allowed to pass therethrough in some cases for the purpose of washing the internal of the tubes and hoses. In medical tubes and medical devices, it is necessary to sterilize at a high temperature. For this reason, it is preferable that the tubes and hoses have heat resistance to an extent that the tubes and hoses are not deformed even at a temperature of around 120° C.

In cases of the medical tubes and the medical devices, they may be used in application of contact with blood in some cases. Especially, the tubes or the like used in a blood circuit or an intravascular catheter are required to have blood compatibility such as nonhemolytic properties and antithrombogenic properties.

Meanwhile, a plasticizer, a softening agent, an extender or the like may be formulated as a raw material for the tube for the purpose of giving the tube flexibility. The components such as a plasticizer, a softening agent, and an extender have a high possibility of being eluted into contents, which is problematic for practical purposes, especially in precision analysis and a medical practice. For instance, vinyl chloride used in the medical tubes and the medical devices contains a large amount of a plasticizer, and it has been confirmed that a plasticizer such as phthalic acid ester is eluted into blood in a blood circuit tube, a blood donation tube or the like, made of vinyl chloride, thereby making it seriously problematic. An oil component is formulated in the compositions described in Literature 8 and Literature 9, so that there is a possibility that the elution of the oil component is generated. Therefore, it is desirable that especially medical tubes and medical devices do not contain an oil component, a plasticizer, a softening agent, an extender or the like.

In addition, in a case where a cross-linking agent, a cross-linking accelerator or the like is contained, since its toxicity is problematic, it is desirable that especially the medical tubes and the medical devices do not contain a cross-linking agent, a cross-linking accelerator or the like.

Specifically, an object of the present invention is to provide a laminate for industrial, foods and medical uses, which has satisfactory abrasion resistance and flexibility, is excellent in transparency, antifouling property, heat resistance and blood compatibility, and is also excellent in safety; a multilayer tube comprising the laminate, which is especially suitably used in a medical device such as a pump tube, an extracorporeal circulation circuit or a blood bag; and a medical device comprising the laminate and/or the multilayer tube.

Specifically, the present invention relates to:
[1] a laminate comprising at least a surface layer (I) and an adjacent layer (II) thereto, characterized in that the surface layer (I) comprises a cross-linked copolymer formed by cross-linking a copolymer prepared by using as monomers at least one vinyl aromatic compound and at least one conjugated diene compound, and the adjacent layer (II) comprises a hydrogenated copolymer formed by hydrogenating a copolymer prepared by using as monomers at least one vinyl aromatic compound and at least one conjugated diene compound;
[2] a multilayer tube comprising the laminate of the above [1]; and
[3] a medical device comprising the laminate of the above [1], and/or the multilayer tube of the above [2].

BEST MODE FOR CARRYING OUT THE INVENTION

One of the great features of the laminate of the present invention resides in that the laminate has at least two layers comprising a surface layer (I) comprising a cross-linked copolymer formed by cross-linking a copolymer prepared by using as monomers at least one vinyl aromatic compound and at least one conjugated diene compound [hereinafter referred to as copolymer (I)], and an adjacent layer (II) comprising a hydrogenated copolymer obtained by hydrogenating a copolymer prepared by using as monomers at least one vinyl aromatic compound and at least one conjugated diene compound [hereinafter referred to as copolymer (II)]. Since the laminate of the present invention has the above constitution, the laminate has satisfactory abrasion resistance and flexibility to an extent that is required in tubes and the like for industrial, food and medical uses, and is also excellent in transparency, antifouling property, heat resistance, blood compatibility and the like. The above surface layer (I) is excellent in properties such as abrasion resistance, flexibility, transparency, antifouling property, heat resistance, blood compatibility and safety, while the adjacent layer (II) is excellent in properties such as flexibility, transparency and molding processibility. In addition, both of the layers have affinity to each other. It is deduced that the desired effects of the present invention are exhibited by synergistically exhibiting the properties of each of the layers because both of the layers are combined so that the layers are adjacent to each other.

The laminate of the present invention has a structure that the surface layer (I) and the adjacent layer (II) mentioned above are adjacent to each other, and that the surface layer (I) forms a layer of the surface (surface layer) of the laminate. Other members, structures, and the like are not particularly limited, so long as the desired effects of the present invention can be exhibited. The method for producing the laminate is not particularly limited, so long as the desired laminate of the present invention is obtained. For instance, it is preferable to produce the laminate by the following two methods.

(1) Method Comprising Preparing a Cross-Linking-Applied Surface Layer (I), and Thereafter Laminating the Surface Layer with Other Layer Raw material monomers and the like are copolymerized by a known method to give a copolymer (I). The resulting copolymer (I) and optionally other resins, and other components such as a plasticizer, a softening agent, and an extender are kneaded and molded by a known method to give a surface layer (I). In a case where other components are not used at all, the copolymer (I) is molded as it is, to give a surface layer (I). Here, the cross-linking of the copolymer (I) (or a kneaded mixture with other components) is carried out in a step after the copolymer (I) is obtained.

Meanwhile, as described above, there is a possibility that other components such as a plasticizer, a softening agent, and an extender, especially a plasticizer, a softening agent and an extender are eluted, for instance, when a laminate is used for a precision analysis or medical use. Especially, there is a possibility that a surface layer (I) is directly contacted with blood or the like, when a laminate is used, for instance, in a medical application or the like. For this reason, it is desirable that the surface layer (I) does not contain any of a plasticizer, a softening agent and an extender. Therefore, in the present invention, a laminate of which surface layer (I) does not contain any of a plasticizer, a softening agent, and an extender is preferable.

As the cross-linking method, two methods can be employed. One method comprises kneading the copolymer (I) with a cross-linking agent (and a cross-linking aid) in a kneading step, to carry out a cross-linking reaction in the step. Another method comprises molding a copolymer (I) (or a kneaded mixture with other components) without using a cross-linking agent (and a cross-linking aid), and thereafter irradiating the molded product with active energy ray to carry out a cross-linking reaction.

The resulting surface layer (I), and an adjacent layer (II) separately similarly prepared by molding a copolymer (II) (or a kneaded mixture with other components) hydrogenated by a known method, and optionally other layers are laminated by a known method as desired, to give a laminate of the present invention.

(2) Method Comprising Laminating Cross-Linking-Unapplied Surface Layer (I) and Other Layer, and Thereafter Carrying Out Cross-Linking Two methods can be employed depending on the cross-linking methods employed. In one method, a cross-linking agent (and a cross-linking aid) are used. In the method, the resulting copolymer (I), a cross-linking agent (and a cross-linking aid) and optionally other components are kneaded, to give a kneaded mixture. In addition, a hydrogenated copolymer (II) (or a kneaded mixture with other components), and optionally other layer components are obtained. These components are not individually molded, but are laminated and molded at once by a known method, with a cross-linking reaction being carried out, to give a laminate of the present invention.

Another method is carried out without a cross-linking agent (and a cross-linking aid). In the method, a copolymer (I) (or a kneaded mixture with other components), a hydrogenated copolymer (II) (or a kneaded mixture with other components) and optionally other layer components are obtained, and these components are not individually molded, but are laminated and molded at once by a known method. After molding, the molded product is irradiated with active energy rays to carry out a cross-linking reaction, to give a laminate of the present invention.

The method for producing a laminate of the present invention exemplified herein includes two methods depending on the lamination method [specifically, an embodiment comprising applying cross-linking to a surface layer (I), and thereafter laminating the surface layer with other layer [the above (1)], and an embodiment comprising laminating a surface layer (I) with other layer, and thereafter carrying out cross-linking [the above (2)]]; and further each of the two methods includes two methods depending on the cross-linking method employed [specifically, an embodiment comprising carrying out cross-linking with a cross-linking agent (and a cross-linking aid), and an embodiment comprising carrying out cross-linking using irradiation of active energy rays without a cross-linking agent (and a cross-linking aid)]. The desired laminate can be produced by any of the methods. As the method for producing a laminate, an embodiment comprising laminating a surface layer (I) with other layer, and thereafter carrying out cross-linking [the above (2)] is preferable, from the viewpoint that the production process is simple. Among them, an embodiment comprising carrying out cross-linking using irradiation of active energy rays without a cross-linking agent (and a cross-liking aid) is more preferable. In the cross-linking agent and the cross-linking aid, their toxicities may become problematic in some cases. For instance, it is desired that the surface layer (I) which has a possibility of directly contacting with blood or the like does not contain a cross-linking agent and a cross-linking aid, when a laminate is used in a medical use or the like. By producing a laminate according to the more preferable embodiment of the method for a producing a laminate, there can be obtained a laminate comprising a surface layer (I) which does not contain a cross-linking agent and a cross-linking aid, wherein the cross-linking is carried out by irradiation of active energy rays. The above laminate is especially useful for medical devices such as medical tubes.

The raw materials, the methods and the like which are used in the production of the laminate of the present invention will be explained below. The copolymer (I) and the copolymer (II) are substantially the same in their raw material compositions, their production methods and the like, except that each of the copolymers is either cross-linked or hydrogenated (serving to suppress cross-linking formation) in the step of preparing the surface layer (I) and the adjacent layer (II). Here, a part of the surface layer (I) may be hydrogenated, or a part of the adjacent layer (II) may be cross-linked, so long as the exhibition of the desired effects of the present invention would not be hindered.

The vinyl aromatic compound used in the present invention includes, for instance, vinyl aromatic monomers such as styrene, α-methylstyrene, 1-vinylnaphthalene, 3-methylstyrene, 4-propylstyrene, 4-cyclohexylstyrene, 4-dodecylstyrene, 2-ethyl-4-benzylstyrene and 4-(phenylbutyl)styrene. These vinyl aromatic compounds can be used alone or in admixture of two or more kinds. Among them, styrene is preferred as the vinyl aromatic compound.

It is preferable that the content of the vinyl aromatic compound in the copolymer (I) is, but not particularly limited to, within the range of from 10 to 40% by weight. When the content of the vinyl aromatic compound is 10% by weight or more, it is preferable because mechanical strength of the surface layer (I) becomes high. In addition, when the content of the vinyl aromatic compound is 40% by weight or less, it is preferable because the surface layer (I) has excellent flexibility.

The conjugated diene compound includes conjugated diene monomers such as butadiene, isoprene, 1,3-pentadiene, and 2,3-dimethyl-1,3-butadiene. These conjugated diene compounds can be used alone or in admixture of two or more kinds. Among them, the conjugated diene compound is preferably butadiene and/or isoprene. It is preferable that the content of the conjugated diene compound in the copolymer (I) is, but not particularly limited to, within the range of from 60 to 90% by weight, in consideration of the preferred embodiment of the content of the above vinyl aromatic compound. When butadiene and isoprene are used as the conjugated diene compounds, the amount proportion of both of the compounds is not particularly limited, so long as the desired effects of the present invention are obtained.

The copolymer (I) in the present invention may be preferably a block copolymer, a random copolymer and a combination thereof of the vinyl aromatic compound and the conjugated diene compound, more preferably a block copolymer. The amount proportion of both of the copolymers in any combination of the block copolymer and the random copolymer is not particularly limited, so long as the desired effects of the present invention are obtained.

The number-average molecular weight as referred to hereinbelow is a value obtained as a number-average molecular weight (Mn) calculated as polystyrene as determined by GPC. Also, the content of 1,2-bonds and 3,4-bonds is simply referred to as content of vinyl bonds.

In a case where the copolymer (I) contains a random copolymer (including a case where the copolymer (I) is composed only of the random copolymer), it is preferable that the random copolymer has a number-average molecular weight of within the range of from 30000 to 500000. In addition, the random copolymer has a content of vinyl bonds of preferably 5% by mol or more, more preferably 40% by mol or more.

The case where the copolymer (I) contains a block copolymer (including a case where the copolymer (I) is composed only of the block copolymer) will be described in detail hereinbelow.

It is preferable that the polymer block comprising a vinyl aromatic compound has a number-average molecular weight of, but not particularly limited to, from 2500 to 50000.

When the conjugated diene compound is isoprene, the polyisoprene block has a content of vinyl bonds of preferably 5% by mol or more, more preferably from 10 to 95% by mol, especially preferably from 50 to 80% by mol, even more preferably from 65 to 80% by mol.

In addition, when the conjugated diene compound is butadiene, the polybutadiene block has a content of vinyl bonds of preferably 5% by mol or more, more preferably 40% by mol or more.

Also, in a case of a copolymer block of a mixture prepared by mixing isoprene and butadiene as the conjugated diene compounds in a ratio of, for instance, from 5/95 to 95/5 (weight ratio), the copolymer block has a content of vinyl bonds of preferably 5% by mol or more, more preferably 40% by mol or more. The polymerization forms of isoprene and butadiene in the copolymer block may be, but not particularly limited to, any of random, block, tapered and other forms.

It is preferable that the polymer block constituted by the conjugated diene compound has a number-average molecular weight of, but not particularly limited to, within the range of from, 22000 to 470000.

The binding form of the block copolymer constituted by the vinyl aromatic compound blocks and the conjugated diene compound blocks may be, but not particularly limited to, linear or branched binding, or any combination thereof. Concrete examples include the binding forms of A(BA)n, (AB)n, and the like, wherein A is a vinyl aromatic compound block, B is a conjugated diene block, and n is an integer of 1 or more. In addition, as the block copolymer constituted by the vinyl aromatic compound blocks and the conjugated diene compound blocks, there can be used those having a stellate [for example, [(AB)mX], wherein X is a residue of a coupling agent, and m is valency of the residue of an integer of 2 or more] molecular structure, obtained by using divinyl benzene, a tin compound, a silane compound or the like as a coupling agent.

As the block copolymers constituted by the vinyl aromatic compound blocks and the conjugated diene compound blocks, those having various kinds of molecular structures mentioned above may be each used alone, or alternatively, may be used as a combination of two or more different kinds of molecular structures, such as a mixture of a triblock type and a diblock type.

It is preferable that the block copolymer constituted by the vinyl aromatic compound blocks and the conjugated diene compound blocks has a number-average molecular weight of within the range of from 30000 to 500000. In addition, the block copolymer has a content of vinyl bonds of preferably 5% by mol or more, more preferably 40% by mol or more.

In the laminate of the present invention, the following embodiments, for instance, are preferable. Specifically, it is preferable that the copolymer in the surface layer (I) and/or the adjacent layer (II) is a block copolymer. In addition, it is preferable that the conjugated diene compound used in the preparation of the copolymer in the surface layer (I) and/or the adjacent layer (II) is isoprene and/or butadiene. Also, it is preferable that the vinyl aromatic compound used in the preparation of the copolymer in the surface layer (I) and/or the adjacent layer (II) is styrene. It is also preferable that the content of the vinyl aromatic compound in the copolymer in the surface layer (I) and/or the adjacent layer (II) is from 10 to 40% by weight.

As the method for preparing a block copolymer, any known preparation methods can be utilized. The method includes, for instance, the following methods (a) to (c): (a) a method comprising polymerizing a vinyl aromatic compound using an alkyllithium compound as a polymerization initiator (which may be hereinafter referred to as an initiator in some cases), and thereafter sequentially polymerizing a conjugated diene compound and a vinyl aromatic compound; (b) a method comprising polymerizing a vinyl aromatic compound and thereafter a conjugated diene compound to give a block copolymer, and coupling the resulting block copolymer with a coupling agent; and (c) a method comprising polymerizing a conjugated diene compound using a dilithium compound as a polymerization initiator, and thereafter sequentially polymerizing a vinyl aromatic compound thereto.

In the method described above, as the alkyllithium compound, which is an initiator, there may be generally used, for instance, a compound of which alkyl group has 1 to 10 carbon atoms. Among them, methyllitium, ethyllithium, pentyllithium, n-butyllithium, s-butyllithium and t-butyllithium are preferred. In addition, the coupling agent for coupling the block copolymer includes, for instance, halogenated compounds such as dichloromethane, dibromomethane, dichloroethane, dibromoethane, dibromobenzene and tin tetrachloride; ester compounds such as phenyl benzoate and ethyl acetate; divinylbenzene; various silane compounds; and the like. Further, the dilithium compound, which is an initiator, includes, for instance, naphthalenedilithium, dilithiohexylbenzene and the like.

The amount of the initiator or coupling agent mentioned above used may be appropriately determined depending upon the molecular weight of the desired block copolymer. Usually, the polymerization initiator may be used within the range of from 0.01 to 0.2 parts by weight, and the coupling agent may be used within the range of from 0.04 to 0.8 parts by weight, based on 100 parts by weight of the entire monomers used in the polymerization.

In addition, the content of vinyl bonds in the conjugated diene compound block can be controlled by using a Lewis base as a cocatalyst upon polymerization. The above Lewis base includes, for instance, ethers such as dimethyl ether, diethyl ether and tetrahydrofuran; glycol ethers such as ethylene glycol dimethyl ether and diethylene glycol dimethyl ether; amine-based compounds such as triethylamine, N,N,N',N'-tetramethyl ethylenediamine (hereinafter simply referred to as TMEDA) and N-methylmorpholin; and the like. It is preferable that the amount of the Lewis base used is, for instance, within the range of from 0.1 to 1000 mol per mol of the lithium atoms in the polymerization initiator.

Upon polymerization, it is preferable to use an organic solvent which is inert to the polymerization initiator as a solvent. As the solvent, it is desired to use an aliphatic hydrocarbon having 6 to 12 carbon atoms such as hexane and heptane, an alicyclic hydrocarbon such as cyclohexane and methylcyclohexane, and an aromatic hydrocarbon such as benzene. It is preferable that the polymerization is carried out usually within the temperature range of from 0° to 80° C. in any of the above polymerization methods (a) to (c) for a reaction time of from 0.5 to 50 hours.

The plasticizer, the softening agent and the extender used as other components include phthalic acid ester-based compounds such as dimethyl phthalate, diethyl phthalate, dibutyl phthalate, diheptyl phthalate, di-2-ethylhexyl phthalate, di-n-octyl phthalate, diisodecyl phthalate, butylbenzyl phthalate, diisononyl phthalate, ethylphthalyl ethyl glycolate, diundecyl phthalate, di-2-ethylhexyl tetrahydrophthalate, di-n-decyl phthalate and ditridecyl phthalate; fatty acid ester-based compounds such as di-2-ethylhexyl adipate, diisobutyl adipate, dibutyl adipate, diisodecyl adipate, dibutyl diglycol adipate, dibutyl diglycol adipate, di-2-ethylhexyl azeleate, dibutyl sebacate and butyl oleate; epoxidated ester-based compounds such as epoxidated soybean oil and di-2-ethylhexyl epoxyhexahydrophthalate; polyester-based compounds such as adipic acid ester; phosphoric ester-based compounds such as trisdichloropropyl phosphate and triphenyl phosphate; trimellitic acid ester-based compounds such as tri-2-ethylhexyl trimellitate and triisodecyl trimellitate; naphthenic oil, paraffin oil, aromatic oils and the like.

In addition, the cross-linking agent and the cross-linking aid include organic peroxides, inorganic peroxides, azo compounds, mono- and disulfides, metal chelates, redox initiators, sulfur, sulfur-containing compounds, vulcanization accelerators, phenolic resins, cross-linking catalysts, quinone oximes, lead oxides and the like. The cross-linking method will be described later.

The other resin and the like include, for instance, monomers other than the vinyl aromatic compound and the conjugated diene compound used in the present invention, and resins other than the copolymers (I) and (II).

For instance, as the constituent of the surface layer (I), there may be formulated a polyfunctional acrylic monomer, a polyfunctional allyl monomer, each of which is a cross-linkable monomer, or a mixed monomer thereof.

The polyfunctional acrylic monomer includes ethylene oxide-modified bisphenol A di(meth)acrylate, 1,4-butanediol di(meth)acrylate, diethylene glycol di(meth)acrylate, dipentaerythritol hexa(meth)acrylate, dipentaerythritol monohydroxypenta(meth)acrylate, caprolactone-modified dipentaerythritol hexa(meth)acrylate, pentaerythritol tri(meth)acrylate, pentaerythritol tetra(meth)acrylate, polyethylene glycol di(meth)acrylate, trimethylolpropane tri(meth)acrylate, ethylene oxide-modified trimethylolpropane tri(meth)acrylate, propylene oxide-modified trimethylolpropane tri(meth)acrylate, tris(acryloxyethyl) isocyanurate, tris(methacryloxyethyl) isocyanurate, and mixtures thereof. Here, (meth)acrylate means acrylate or methacrylate.

The polyfunctional allyl monomer includes triallyl cyanurate, triallyl isocyanurate, diallyl phthalate, diallylbenzene phosphonate, and mixtures thereof.

The resin other than the copolymers (I) and (II) includes, for instance, other polymers such as hydrogenated polyisoprenes, hydrogenated polybutadienes, hydrogenated styrene-butadiene copolymers, hydrogenated styrene-isoprene copolymers, butyl rubber, polyisobutylenes, polybutenes, ethylene-propylene rubbers, polyolefin resins (for instance, polyethylenes, polypropylenes, ethylene-α-olefin copolymers and the like), ethylene-vinyl acetate copolymers, ethylene-methacrylic acid copolymers, ethylene-acrylic acid copolymers, and ionomers thereof, and ethylene-ethyl acrylate copolymers.

In the present invention, the hydrogenated copolymer (II) is used as a constituent of the adjacent layer (II). When a polyolefin resin is used as other resin, it is preferable because the hydrogenated copolymer (II) and the polyolefin resin are easily compatible to each other, and their mixture has transparency. In addition, in an adjacent layer (II) made only of the hydrogenated copolymer (II) formed by a molding method such as extrusion molding or injection molding, the copolymer may be oriented to affect the flexibility in some cases. However, by mixing with the polyolefin resin, it is preferable because the orientation is suppressed. There is generally a tendency that a polyolefin resin is insufficient in flexibility, so that its molded article becomes hard when formulated in a large amount. Therefore, the amount of the polyolefin resin is preferably 40% by weight or lower, more preferably 30% by weight or lower, even more preferably 20% by weight or lower. Therefore, in the present invention, the adjacent layer (II) preferably comprises 60 to 100% by weight of the hydrogenated copolymer (II) and 0 to 40% by weight of the polyolefin resin, and more preferably comprises 70 to 100% by weight of the hydrogenated copolymer (II) and 0 to 30% by weight of the polyolefin resin, and even more preferably comprises 80 to 100% by weight of the hydrogenated copolymer (II) and 0 to 20% by weight of the polyolefin resin.

Among the polyolefin resins, especially a polypropylene-based resin is preferable. As the polypropylene-based resin (resin containing polypropylene), known ones can be used, which may be any of homopolypropylene, random polypropylene and block polypropylene. In addition, the polypropylene-based resins may be used alone or in combination of two or more kinds. The polypropylene-based resin has a melt viscosity such that the melt flow rate (MFR) is within the range of from 0.1 to 500 g/10 minutes, more preferably within the range of from 0.1 to 200 g/10 minutes, when determined at 230° C. and a load of 2160 g in accordance with ASTM D-1238, from the viewpoints of the moldability and the mechanical properties.

Furthermore, as other components, various additives such as an antioxidant, an ultraviolet absorbent, a photostabilizer, a colorant and a crystal nucleating agent can be used. Usually, the amount of these additives formulated is, but not particularly limited to, for instance, when formulated to the surface layer (I) or (II), appropriately within the range of from 0.01 to 5 parts by weight, based on 100 parts by weight of the copolymer (I) or (II) [or the mixture of a copolymer (I) or (II) and other resins and other components].

When the optional components as described above are used in the production of the laminate of the present invention, the amount to be formulated is not particularly limited so long as the exhibition of the desired effects of the present invention would not be hindered.

Kneading (or mixing) of the copolymer (I), or the hydrogenated copolymer (II) obtained by hydrogenation according to the method described later, and other resins described above, and other components can be carried out with a kneading machine such as a single-screw extruder, a twin-screw extruder, a kneader, a Banbury mixer or a roller. Here, as mentioned above, when the copolymer (I) (or a mixture with other resins and other components) is cross-linked in the kneading step, kneading is carried out with a cross-linking agent (and a cross-linking aid) added as other component. Such embodiment will be described in detail later.

Other layer besides the surface layer (I) and the adjacent layer (II) (which may be referred to as a layer (III) in some cases; the layer (III) comprises one or more layers), is not particularly limited so long as the layer is formed by components which would not hinder the exhibition of the desired effects of the present invention. The number of the layers is arbitrary, as desired.

Other layer can be appropriately produced by a known method in accordance with, for instance, the method described in the present specification. Alternatively, one which is commercially available can be used.

Since the conjugated diene compound which is a constituent of the surface layer (I) in the present invention has an unsaturated group, a known cross-linking method can be used for the cross-linking of the copolymer (I) constituting the surface layer (I). The methods include, for instance, a method using a radical generator, a method using sulfur or a sulfur-containing compound, a resin cross-linking method, a quinoid cross-linking method, a method using active energy rays and the like.

The radical generator used in the method using a radical generator is a so-called a radical polymerization initiator, and includes organic peroxides such as hydroperoxides, dialkyl peroxides, diacyl peroxides, peroxy ester and ketone peroxides; inorganic peroxides such as hydrogen peroxide, persulfates and metal oxides; azo compounds; mono- and disulfides; metal chelates; redox initiators and the like.

Preferred examples of the hydroperoxide include t-butyl-hydroperoxide, cumene hydroperoxide, 2,5-dimethylhexane-2,5-dihydroperoxide and the like. Preferred examples of the dialkyl peroxide include di-t-butyl peroxide, t-butylcumyl peroxide, dicumyl peroxide, α,α'-bis(t-butylperoxy)-p-diisopropylbenzene, 2,5-dimethyl-2,5-di(t-butylperoxy)hexane, 2,5-dimethyl-2,5-di(t-butylperoxy)hexyne-3 and the like. Preferred examples of the diacyl peroxide include acetyl peroxide, succinic acid peroxide, benzoyl peroxide and the like. Preferred examples of the peroxy ester include t-butyl peroxyacetate, t-butyl peroxyisobutyrate, t-butyl peroxyisopropylcarbonate and the like. Preferred examples of the ketone peroxide include methyl ethyl ketone peroxide, cyclohexanone peroxide and the like.

These radical generators are usually used within the range of preferably from 0.01 to 15 parts by weight, more preferably from 0.05 to 10 parts by weight, based on 100 parts by weight of the conjugated diene compound.

As the cross-linking method, a known method is applied. For instance, the method includes a method comprising heating and melting a polymer block constituted by a vinyl aromatic compound and a conjugated diene compound, a radical generator, and other resins to be added as desired (for instance, thermoplastic resins and the like as mentioned above), and mixing the components. The heating temperature is preferably from 140° to 220° C., and the melting and mixing (kneading) can be carried out in a batch process or a continuous process with an apparatus such as an extruder, a kneader, a roller or a plastograph. The cross-linking is progressed by the above kneading process.

The sulfur and the like used in the method using sulfur or a sulfur-containing compound include, for instance, sulfur and sulfur monochloride, sulfur dichloride and the like. The amount of the sulfur or the sulfur-containing compound is preferably from 0.1 to 20 parts by weight, more preferably from 0.2 to 10 parts by weight, based on 100 parts by weight of the conjugated diene compound. In order to carry out cross-linking using the sulfur or the sulfur-containing compound, a vulcanization accelerator is used together therewith. Examples of the vulcanization accelerator include thiazoles such as N,N-diisopropyl-2-benzothiazole-sulfonamide, 2-mercaptobenzothiazole and 2-(4-morpholinodithio)benzothiazole; guanidines such as diphenyl guanidine and triphenyl guanidine; aldehyde-amine-based compounds or aldehyde-ammonia-based compounds such as butyl aldehyde-aniline reaction products and hexamethylenetetramine-acetoaldehyde reaction products; imidazolines such as 2-mercaptoimidazoline; thioureas such as thiocarbanilide, diethylurea, dibutylthiourea, trimethylthiourea and diorthotolylthiourea; thiuram mono- or polysulfides such as tetramethyl thiuram monosulfide, tetramethyl thiuram disulfide and pentamethylene thiuram tetrasulfide; dithiocarbamates such as zinc dimethyl dithiocarbamate, zinc ethylphenyl dithiocarbamate, sodium dimethyl dithiocarbamate, selenium dimethyl dithiocarbamate and tellurium diethyl dithiocarbamate; xanthogenates such as zinc dibutyl xanthogenate; organic peroxides; zinc flower and the like. These vulcanization accelerators may be used alone or in combination of two or more kinds. The amount of the vulcanization accelerator is preferably from 0.05 to 30 parts by weight, more preferably from 0.1 to 20 parts by weight, even more preferably from 0.2 to 10 parts by weight, based on 100 parts by weight of the conjugated diene compound.

The cross-linking method includes, for instance, a method comprising kneading a polymer block constituted by a vinyl aromatic compound and a conjugated diene compound, sulfur or a sulfur-containing compound, a vulcanization accelerator, a radical generator, and other resin (for instance, the above thermoplastic resins and the like) added as desired with a mixer such as a roller or a Banbury mixer at a temperature of preferably from 50° to 250° C., more preferably from 80° to 200° C., and thereafter keeping the mixture at a temperature of preferably 60° C. or higher, more preferably from 90° to 250° C. for preferably 1 minute to 2 hours, more preferably 5 minutes to 1 hour to form a cross-linking.

In the resin cross-linking method, a phenolic resin such as an alkylphenol resin or a brominated alkylphenol resin is used as a cross-linking agent, and stannous chloride, ferric chloride, an organosulfonic acid, polychloroprene, chlorosulfonated polyethylene or the like is used as a cross-linking catalyst. The amount of the cross-linking agent is preferably from 1 to 30 parts by weight, more preferably from 5 to 20 parts by weight, and the amount of the cross-linking catalyst is preferably from 0.1 to 10 parts by weight, more preferably from 0.5 to 5 parts by weight, based on 100 parts by weight of the conjugated diene compound. The cross-linking temperature is preferably from 100° to 250° C., more preferably from 130° to 220° C.

In the quinoid cross-linking method, as a cross-linking agent, a combination of p-quinone dioxime and lead dioxide, a combination of p,p'-dibenzoylquinone dioxime and trilead tetroxide, or the like is used. The amount of the quinone oxime is preferably from 0.1 to 10 parts by weight, more preferably from 0.5 to 5 parts by weight, and the amount of lead oxides is preferably from 0.1 to 15 parts by weight, more preferably from 0.5 to 10 parts by weight, based on 100 parts by weight of the conjugated diene compound. The cross-linking temperature is preferably from 90° to 250° C., more preferably from 110° to 220° C.

As active energy rays used in the cross-linking method using active energy rays, radioactive rays such as α-rays, β-rays, γ-rays, X-rays, electron beams, positron beams, neutron beams, ultraviolet rays (UV) and the like are preferable, among which γ-rays and electron beams are more preferable, and electron beams are even more preferable. These radioactive rays may be used in combination of two or more kinds. The irradiation conditions for electron beam irradiation are, but not particularly limited to, for instance, acceleration energy of preferably 150 keV or higher, more preferably 3000 keV or higher, and an irradiation dose of preferably from 20 to 600 kGy, more preferably from 100 to 600 kGy, even more preferably from 200 to 450 kGy. Preferably, the irradiation is carried out, but not particularly limited to, in an atmosphere of an inert gas such as nitrogen or argon or in vacuum. In addition, an organic peroxide, sulfur or a sulfur-containing compound, or a vulcanization accelerator can be used together therewith.

The irradiation of the active energy rays is carried out after the copolymer (I) (or a kneaded mixture with other components) is molded in the method of the above (1), whereas the irradiation of the active energy rays is carried out after a kneaded mixture of the constituents of each layer is laminated and molded in the method of the above (2). By carrying out the irradiation, the cross-linking is formed in the copolymer (I) constituting the surface layer (I). However, when the multilayer tube or the medical device of the present invention is produced, the formation of the cross-linking in the surface layer (I) at the stage of the production of a laminate used in the production of the multilayer tube or the medical device is not necessarily required. For instance, the cross-linking may be formed by molding a laminate and a multilayer tube, and thereafter irradiating the laminate and the multilayer tube with active energy rays. When the cross-linking is carried out only by the active energy rays without containing a cross-linking agent and a cross-linking aid, it is especially preferable in the medical device since there is no problem of toxicity of the cross-linking agent and the cross-linking aid. In the case of the medical device, the timing of irradiating the active energy rays may be at a stage of parts (a laminate, a multilayer tube or the like) before assembling, in the course of assembling, or at a stage of final assembling.

The degree of cross-linking of the surface layer (I) can be evaluated by using "gel fraction" as an index.

The polymer which is completely dissolved in a solvent such as tetrahydrofuran or toluene before cross-linking becomes insoluble depending on the degree of cross-linking after the cross-linking. The gel fraction is obtained as a percentage (%) of a weight of the polymer of an insoluble part when the polymer after cross-linking is immersed in a specified solvent divided by a weight before immersion in the solvent. In the present invention, since a laminate having more excellent property such as abrasion resistance is obtained, the gel fraction of the copolymer (I) constituting the surface layer (I) is preferably 60% or higher, more preferably 70% or higher.

On the other hand, the hydrogenation of the copolymer (II) which is a constituent of the adjacent layer (II) can be carried out, for instance, by a known method such as a method comprising reacting hydrogen in a molecular state with the copolymer using a known hydrogenation catalyst in a state dissolved in a solvent inert to a reaction. The hydrogenation catalyst used herein includes a heterogeneous catalyst in which a metal such as Raney nickel, Pt, Pd, Ru, Rh or Ni is supported by a carrier made of carbon, alumina, diatomaceous earth or the like; a Ziegler catalyst comprising a combination of an organometallic compound composed of the Group VIII metal such as nickel or cobalt, with an organoaluminum compound such as triethylaluminum or triisobutylaluminum, or an organolithium compound; a metallocene catalyst comprising a combination of a bis(cyclopentadienyl) compound of a transition metal such as titanium, zirconium or hafnium, with an organometallic compound composed of lithium, sodium, potassium, aluminum, zinc, magnesium or the like.

The hydrogenation is usually carried out at a hydrogen pressure of preferably within the range of from normal pressure to 20 MPa, and a reaction temperature of preferably within the range of from normal temperature to 250° C. Usually, the reaction time is preferably from 0.1 to 100 hours. The hydrogenated copolymer (II) prepared by hydrogenation is obtained by (i) solidifying a reaction mixture with methanol or the like, and thereafter heating the residue or drying the residue under a reduced pressure, (ii) pouring a reaction mixture in boiling water to remove the solvent by azeotropic treatment, thereby carrying out a so-called steam stripping, and thereafter heating the residue or drying the residue under a reduced pressure, and the like.

The hydrogenated copolymer (II) has a reduced number of cross-linkable unsaturated groups as compared to that before the hydrogenation. For instance, in the method of the above (2), the formation of the cross-linking is not substantially generated, even when the cross-linking is carried out by irradiation of active energy rays after molding. For this reason, in the laminate of the present invention, the adjacent layer (II) can maintain an excellent flexibility. Specifically, it is preferable that the hydrogenation ratio is 80% or higher, from the viewpoint of maintenance of the flexibility. Here, the hydrogenation ratio can be calculated by determining iodine values of the copolymer (II) before and after the hydrogenation, and obtaining the ratio from the found values.

The molding of the constituents of each layer can be carried out sequentially [in the case of the method of the above (1)] or simultaneously [in the case of the method of the above (2)] by a given molding method such as (co) extrusion molding, multicolor injection molding, insert molding, press molding, laminate molding, vacuum molding, pressure molding, inflation molding or blow molding. By carrying out cross-linking formation according to the method using a radical generator (excluding a method using active energy rays), the method using sulfur or a sulfur-containing compound, the resin cross-linking method, or the quinoid cross-linking method, or carrying out cross-linking formation according to the method using active energy rays at the same time as molding, and adjusting the molding temperature and time, a sufficient cross-linking can be obtained at the same time as molding. When a sufficient cross-linking is not obtained during molding, sufficient cross-linking can be formed by further subjecting the molded product to a heat treatment (for instance, keeping at 50° to 120° C.) after molding.

In the case of the method of the above (1), the laminate of the present invention is obtained by, for instance, adhering the obtained surface layer (I) together with the adjacent layer (II) and optionally other layer(s) sequentially by a method such as adhesion and welding. On the other hand, the laminate of the present invention is obtained at the same time as molding according to the method of the above (2).

Since the surface layer (I) is cross-linked, the surface layer has excellent strength. In addition, since the layer is highly excellent in flexibility and further the adjacent layer (II) is flexible, a laminate as a whole becomes tough and flexible, thereby making it useful in applications requiring abrasion resistance and flexibility (for instance, a pump tube, a medical device) and the like. In addition, the adjacent layer (II) has affinity with the surface layer (I), whereby the surface layer is less likely to be peeled off when the laminate is frictionized. Further, in the laminate of the present invention, its flexibility can be also appropriately adjusted by adjusting a thickness of the surface layer (I). For instance, when the thickness of the surface layer (I) is made thinner, the thickness of the cross-linked portion becomes thinner, and consequently the laminate becomes more flexible. The surface layer (I) has a thickness, but not particularly limited to, of preferably from 0.01 to 500 μm, more preferably from 0.1 to 300 μm, still more preferably from 1 to 100 μm. The thickness of the adjacent layer (II) is, but not particularly limited to, preferably from 0.1 μm to 20 mm, more preferably from 1 μm to 10 mm.

The laminate of the present invention has excellent transparency. For instance, the contents can be easily observed when used as a tube. Since a surface layer (I) has does not have adhesiveness, whereby dusts or foreign substances are not adhered thereto, the laminate of the present invention is excellent in antifouling property. In addition, the surface layer (I) has a little decrease in storage modulus and is excellent in heat resistance even at a temperature equal to or higher than a glass transition point of the copolymer (I) before cross-linking. For instance, the laminate is preferable in medical applications, because the laminate can withstand high-pressure steam sterilization, and has no problem associated with residual ethylene oxide gas. Alternatively, a sterilizing method such as γ-ray sterilization can be applied. Further, the laminate exhibits non-hemolysis and is also excellent in blood compatibility.

Therefore, it is preferable as the laminate of the present invention that one surface layer or both of the surface layers are constituted by the surface layer (I). Especially, when both of the surface layers are constituted by the surface layer (I), the desired effects of the present invention such as abrasion resistance, transparency, antifouling property, heat resistance and blood compatibility can be exhibited on both of the surface layers. This embodiment is especially suitable for a tube, a hose or the like comprising the laminate of the present invention.

Examples of the laminate of the present invention include a multilayer film, a multilayer sheet, a multilayer tube, a multilayer fiber, a multilayer balloon a multilayer molded article and the like.

The multilayer tube of the present invention comprising the laminate of the present invention is obtained immediately after the above molding step, or by appropriately processing the laminate according to a known method. The multilayer tube has flexibility, and is also excellent in abrasion resistance. For instance, there is little change in a pumping amount, and abrasion or cracks of the tube are not generated, even when a pumping using a tube pump is continued for a long period of time. The multilayer tube in which an innermost layer and an outermost layer are made of the surface layer (I) is preferable because both of the innermost layer and the outermost layer are less likely to be damaged even if frictionized by a tube pump. In addition, the multilayer tube is excellent in transparency, and the contents are clearly visible. Further, the multilayer tube has satisfactory heat resistance and blood compatibility.

Also, the present invention provides a medical device comprising the laminate and/or the multilayer tube mentioned above. Since the laminate and the multilayer tube of the present invention have the above properties, for instance, there is obtained excellent medical devices such as catheters such as indwelling catheters and balloon catheters, and artificial blood vessels, blood circuits, blood bags, syringes, artificial dialyzers, blood component separators, artificial lungs, and wound covering materials, which are excellent in flexibility, abrasion resistance, transparency, antifouling property, heat resistance and blood compatibility. In addition, the laminate and the multilayer tube of the present invention are useful for various applications requiring flexibility, abrasion resistance, transparency, antifouling property and heat resistance thereof. For instance, films, sheets, buttons, tubes, hoses and the like for industrial or food uses can be provided. These medical devices, films and the like for industrial, food and other uses can be produced according to a known method by using the laminate and the multilayer tube of the present invention as all or a part of their constituents, as desired.

EXAMPLES

The present invention will be described more specifically by referring to the following Examples without intending to limit the present invention thereto. The determinations for the content of styrene, the number-average molecular weight, the content of vinyl bonds, the hydrogenation ratio, and the elastic modulus, and the evaluation methods for the abrasion resistance, the transparency, the antifouling property, the heat resistance and the blood compatibility in Examples were carried out in accordance with the following methods.

(Content of Styrene)

The content was calculated from the weight (g) of each monomer component used in the polymerization.

(Number-Average Molecular Weight)

The number-average molecular weight (Mn) calculated as polystyrene was obtained by a GPC determination.

(Content of Vinyl Bonds)

A block copolymer before the hydrogenation was dissolved in a deuterated chloroform ($CDCl_3$), and $^1$H-NMR spectrum was determined. The content of vinyl bonds (% by mol) was calculated from the size of the peak corresponding to 1,2-bonds or 3,4-bonds.

(Hydrogenation Ratio)

Iodine values of a block copolymer before and after the hydrogenation were determined, and the hydrogenation ratio (%) was calculated from the values obtained.

Hydrogenation Ratio (%)=[1−(Iodine Value of Block Copolymer After Hydrogenation/Iodine Value of Block Copolymer Before Hydrogenation)]×100

(Elastic Modulus)

The elastic modulus was determined using a No. 2 test piece having a thickness of 2 mm as prescribed in JIS K7113 at a test speed of 100 mm/min.

(Abrasion Resistance)

In the case of a tube, a tube having an outer diameter of 12 mm, an inner diameter of 8 mm and a length of 50 cm was set on a blood pump (DKP-01, manufactured by NIKKISO Co., Ltd.). The damages on the tube surface after operating the pump for 4 hours at a pumping rate of 300 mL/minute were observed, and evaluated according to the following evaluation criteria.

Figure 1:
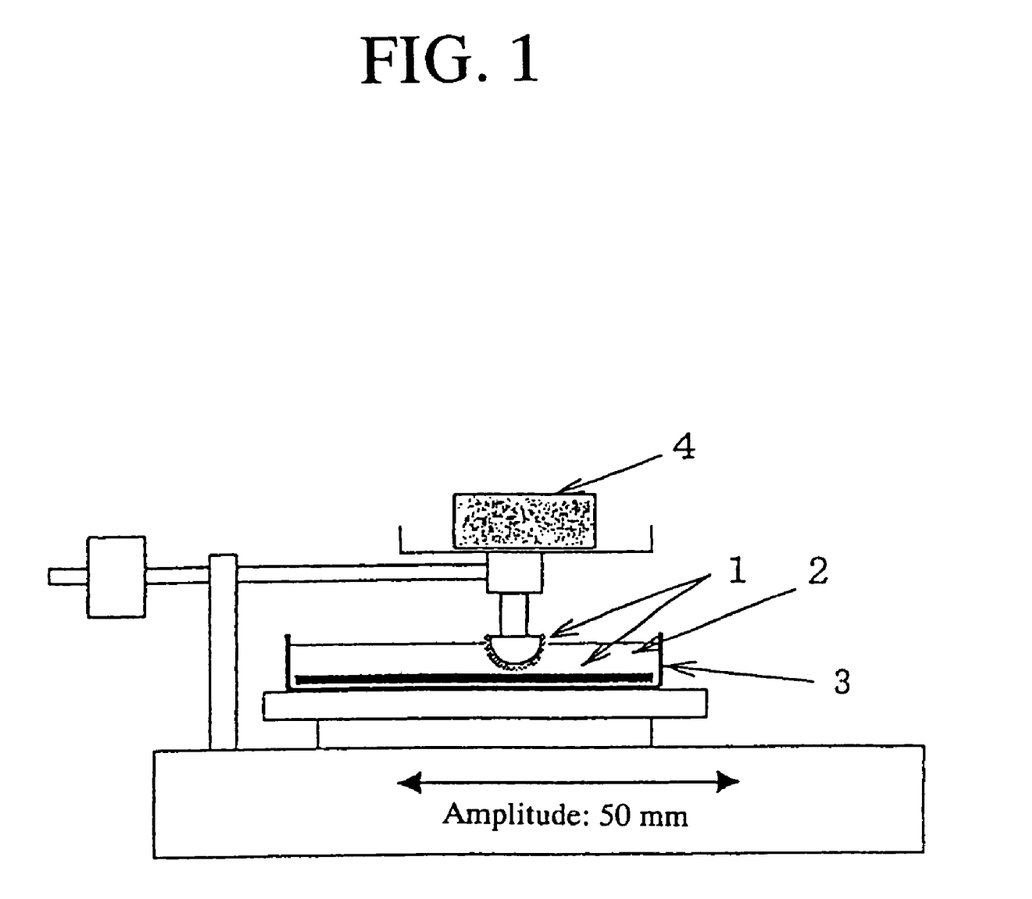
FIG. 1 is a schematic view showing an apparatus for evaluating the abrasion resistance of the sheet. In the figure, 1 is a layer (1) of the sheet, 2 is distilled water, 3 is an aluminum tray and 4 is a weight, respectively.

In the case of a sheet, the abrasion resistance was evaluated with an apparatus as shown in FIG. 1. In the figure, both surfaces of a layer (I) of a sheet represented by 1 were overlaid so as to be contacted linearly, a weight 4 of 5 kg was placed thereon, distilled water 2 was placed in an aluminum tray 3, and damages on the sheet surface were observed after the surfaces were rubbed together in a horizontal direction at an amplitude of 50 mm and a period of 1.3 seconds back-and-forth for 700 times, and evaluated according to the following evaluation criteria.

[Evaluation Criteria]
○: No defects such as damages and scratches are found on the surface of a tube or a sheet.
x: Defects such as damages and scratches are found on the surface of a tube or a sheet.

(Transparency)
In the case of a tube, the contents of the tube were observed from the outside, and evaluated according to the following evaluation criteria.

[Evaluation Criteria]
○: Contents can be seen clearly.
x: Contents cannot be seen clearly.
In the case of a sheet, a sheet having a thickness of 1 mm was produced, and a Haze value was determined with a Haze meter as prescribed in JIS-K7105. When the Haze value was less than 10%, the sheet was evaluated to have a satisfactory transparency (○). On the other hand, when the Haze value was 10% or more, the sheet was evaluated not to have a satisfactory transparency (x).

(Antifouling Property)
In the case of a tube, an inner surface and an outer surface were touched by a hand, and in the case of a sheet, the surface layer (I) was touched by a hand, and evaluated according to the following evaluation criteria.

[Evaluation Criteria]
○: No stickiness is recognized, thereby having satisfactory antifouling property.
x: Stickiness is recognized, thereby having unsatisfactory antifouling property.

(Heat Resistance)
The heat resistance was evaluated by comparing storage moduli (logE') (Pa) of block copolymers of test pieces before and after cross-linking each having a length of 20 mm, a width of 5 mm and a thickness of 1 mm, wherein the storage modulus was determined under the conditions of tensile mode, a frequency of 1 Hz, an amplitude of 3 mm, and a temperature of −80° to 250° C. in a dynamic viscoelasticity measuring apparatus DVE-V4FT Rheospectoler manufactured by Rheology Co., Ltd.

(Blood Compatibility)
A hemolyzation test was carried out according to the Notification No. 99 "Guideline for Necessary Biological Test for Filing Approval of Manufacture (Importation) of Medical Device" by Manager of Department of Development of Medical Devices, Pharmaceutical Bureau, Ministry of Public Welfare. As the extraction conditions of a test solution, there were adopted an extraction temperature: 121° C., an extraction time: 1 hour, a liquor ratio: 10 to 12 mL of a physiological saline per 60 cm² of a surface area of a test piece. When the hemolysis ratio was within 2%, the test piece was evaluated to have blood compatibility (○). The hemolysis ratio was obtained by the following equation (1).

Hemolysis Ratio (%)={[(Absorbance of Test Solution)−(Absorbance of Blank Test Solution)]/[(Absorbance of Positive Control)−(Absorbance of Blank Test Solution)]}×100    (1)

Preparation Example 1

Preparation of Block Copolymer

In a pressure-resistant container replaced with dry nitrogen, styrene was polymerized at 60° C. using cyclohexane as a solvent, and s-butyllithium as a polymerization initiator, TMEDA was added thereto as a Lewis base, and thereafter isoprene and styrene were successively polymerized to give a styrene-isoprene-styrene block copolymer (the block copolymer obtained in Preparation Example 1 being hereinafter simply referred to as a block copolymer 1). The content of styrene, the number-average molecular weight and the content of vinyl bonds of the resulting block copolymer 1 are shown in Table 1.

Preparation Example 2

Preparation of Block Copolymer

A styrene-(isoprene/butadiene)-styrene block copolymer (the block copolymer obtained in Preparation Example 2 being hereinafter simply referred to as a block copolymer 2) was prepared by successively polymerizing styrene, a mixture of isoprene and butadiene [isoprene/butadiene=60/40 (weight ratio)], and styrene using s-butyllithium and TMEDA in a solvent of cyclohexane in the same manner as in Preparation Example 1. The content of styrene, the number-average molecular weight and the content of vinyl bonds of the resulting block copolymer 2 are shown in Table 1.

Preparation Example 3

Preparation of Block Copolymer

A styrene-butadiene-styrene block copolymer (the block copolymer obtained in Preparation Example 3 being hereinafter simply referred to as a block copolymer 3) was prepared by successively polymerizing styrene, butadiene and styrene using s-butyllithium and TMEDA in a solvent of cyclohexane in the same manner as in Preparation Example 1. The content of styrene, the number-average molecular weight and the content of vinyl bonds of the resulting block copolymer 3 are shown in Table 1.

Preparation Example 4

Preparation of Hydrogenated Block Copolymer

In a pressure-resistant container replaced with dry nitrogen, styrene was polymerized at 60° C. using cyclohexane as a solvent and s-butyllithium as a polymerization initiator, TMEDA was added thereto as a Lewis base, and thereafter isoprene and styrene were successively polymerized thereto to give a styrene-isoprene-styrene block copolymer. The resulting block copolymer was hydrogenated in cyclohexane under a hydrogen atmosphere at a hydrogen pressure of 2 MPa using Pd/C as a catalyst, to give a hydrogenated block copolymer (the hydrogenated block copolymer obtained in Preparation Example 4 being hereinafter simply referred to as a block copolymer 4). The content of styrene, the number-average molecular weight, the content of vinyl bonds and the hydrogenation rate of the resulting block copolymer 4 are shown in Table 1.

TABLE 1

| | Block Copolymer | Molecular Structure (Note) | Content of Styrene (% by wt.) | Number-Average Molecular Weight ($\times 10^4$) | Content of Vinyl Bonds (% by mol) | Hydrogenation Ratio (%) |
|---|---|---|---|---|---|---|
| Prep. Ex 1 | 1 | A-B-A | 20 | 10.3 | 75 | — |
| Prep. Ex 2 | 2 | A-C-A | 20 | 10.8 | 60 | — |
| Prep. Ex 3 | 3 | A-D-A | 20 | 10.5 | 72 | — |
| Prep. Ex 4 | 4 | A-B-A | 20 | 10.3 | 55 | 90 |

(Note):
A: Polystyrene Block
B: Polyisoprene Block
C: Poly(isoprene.butadiene) Block
D: Polybutadiene Block Examples 1 to 3 and Comparative Examples 1 to 2

Multilayer sheets were produced at a setting of 170° to 200° C. with a coextrusion multilayer sheet molding machine (manufactured by TOSHIBA MACHINE Co., Ltd.) using the block copolymers 1 to 4 obtained in Preparation Examples 1 to 4 and random type polypropylene [J215W (trade name), manufactured by Grand Polymer Co., Ltd.] in accordance with Table 2. Each of the thicknesses of the surface layer (I) and the layer (III) was set at 0.1 mm, and a thickness of a whole sheet was set at 1 mm. Each of the resulting multilayer sheets was placed in a polyamide bag charged with nitrogen, and the bag was sealed. Cross-linking was applied to each of the sheets by the irradiation with an electron beam at acceleration energy of 4.6 MeV, and an irradiation dose under the conditions as shown in Table 2. The abrasion resistance, the transparency, the antifouling property and the blood compatibility of these multilayer sheets were evaluated. The results are shown in Table 2.

Comparative Example 3

A monolayer sheet having a thickness of 1 mm was produced at 160° C. using polyvinyl chloride with a heat-pressing machine. The abrasion resistance, the transparency, the antifouling property and the blood compatibility of this sheet were evaluated. The results are shown in Table 2.

TABLE 2

| | Ex. 1 | Ex. 2 | Ex. 3 | Comp. Ex. 1 | Comp. Ex. 2 | Comp. Ex. 3 |
|---|---|---|---|---|---|---|
| Surface Layer (I) | Block Copolymer 1 | Block Copolymer 2 | Block Copolymer 3 | Block Copolymer 1 | Block Copolymer 4 | Polyvinyl Chloride |
| Layer (II) | Block Copolymer 4 (90 wt %) + PP (10 wt %) | Block Copolymer 4 (60 wt %) + PP (40 wt %) | Block Copolymer 4 (80 wt %) + PP (20 wt %) | Block Copolymer 4 (90 wt %) + PP (10 wt %) | Block Copolymer 4 (90 wt %) + PP (10 wt %) | None |
| Layer (III) | None | Block Copolymer 2 | Block Copolymer 3 | None | None | None |
| Irradiation Dose (kGy) | 250 | 300 | 350 | 0 | 250 | 0 |
| Abrasion Resistance Surface Layer (I) | ○ | ○ | ○ | X | X | X |
| Transparency Haze Value (%) | 2.6 | 4.7 | 3.3 | 2.6 | 2.5 | 2.3 |
| Evaluation | ○ | ○ | ○ | ○ | ○ | ○ |
| Antifouling Property | ○ | ○ | ○ | X | X | ○ |
| Blood Compatibility Hemolysis Ratio (%) by Surface Layer (I) | 0.1 | 0.2 | 0.2 | 1.0 | 0.1 | 0.5 |
| Evaluation | ○ | ○ | ○ | ○ | ○ | ○ |

*PP: Polypropylene

As shown in Table 2, the multilayer sheets of Examples 1 to 3 were excellent in abrasion resistance, transparency, antifouling property and blood compatibility, while the sheet of Comparative Example 1 without being irradiated with an electron beam had no cross-linking formation, and was inferior in abrasion resistance and antifouling property In addition, in a case where there was hardly any carbon-carbon double bonds due to the hydrogenation as in Comparative Example 2, cross-linking did not take place even when irradiated with an electron beam, and the sheet was inferior in abrasion resistance and antifouling property as in Comparative Example 1. On the other hand, the polyvinyl chloride sheet of Comparative Example 3 was inferior in abrasion resistance.

Examples 4 to 6 and Comparative Examples 4 to 6

A multilayer tube and a monolayer tube were produced at a setting of 170° to 200° C. with a coextrusion multilayer tube molding machine (manufactured by Ikegai Tekko) using the block copolymers 1 to 4 obtained in Preparation Examples 1 to 4, random type polypropylene [J215W (trade name), manufactured by Grand Polymer Co., Ltd.] and a low-density polyethylene (density: 0.90, MI=2) in accordance with Table 3. Each of the thicknesses of the surface layer (I) (inner layer) and the layer (III) (outer layer) was set at 0.1 mm, an outer diameter was set at 12 mm, and an inner diameter was set at 8 mm. Each of the resulting tubes was placed in a polyamide bag charged with nitrogen, and the bag was sealed. Cross-linking was applied to each of the tubes by the irradiation with an electron beam at acceleration energy of 4.6 MeV, and an irradiation dose under the conditions as shown in Table 3. The abrasion resistance, the transparency, the antifouling property and the blood compatibility of these tubes were evaluated. In addition, the elastic modulus of a resin layer constituting the layer (II) was determined for Examples 4 to 6, and Comparative Examples 4 and 5, and the elastic modulus of a resin layer constituting the surface layer (I) was determined for Comparative Example 6. The results are shown in Table 3.

As shown in Table 3, the multilayer tubes of Examples 4 to 6 were excellent in abrasion resistance, transparency, antifouling property and blood compatibility, while the tube of Comparative Example 4 without being irradiated with an electron beam had no cross-linking formation, and was inferior in abrasion resistance and antifouling property In a case where there was hardly any carbon-carbon double bond due to the hydrogenation as in Comparative Example 5, cross-linking did not take place even when irradiated with an electron beam, and the tube was inferior in abrasion resistance and antifouling property as in Comparative Example 4. In the multilayer tubes of Examples 4 to 6, the layer (II) (intermediate layer) occupying a majority of the tube was flexible (low values of elastic modulus), so that a blood pump operated normally. Contrary, the monolayer tube of Comparative Example 6 was rigid (high value of elastic modulus), so that the blood pump did not operate normally.

Comparative Examples 7 to 12

The following materials were used: 12-nylon [UBE Nylon 3024B (trade name), manufactured by UBE INDUSTRIES, LTD.], a polyamide elastomer [Pebax 6333 (trade name), manufactured by Toray Industries, Inc.], polybutylene terephthalate [TEIJIN PBT C7030 (trade name), manufactured by Teijin Limited], an aromatic polyester-aliphatic polyester copolymer [PELPRENE S2001 (trade name), manufactured by TOYOBO CO., LTD.], low-density polyethylene (density 0.90, MI=2), an ethylene-vinyl acetate copolymer (vinyl acetate: 15% by weight, MI=1), a silane-grafted polyethylene (silane content=40% by weight), a silicone oil [KF96 (trade name), manufactured by Shin-Etsu

TABLE 3

|  | Ex. 4 | Ex. 5 | Ex. 6 | Comp. Ex. 4 | Comp. Ex. 5 | Comp. Ex. 6 |
| --- | --- | --- | --- | --- | --- | --- |
| Surface Layer (I) (Inner Layer) | Block Copolymer 1 | Block Copolymer 2 | Block Copolymer 3 | Block Copolymer 1 | Block Copolymer 4 | Low-Density PE |
| Layer (II) (Intermediate Layer) | Block Copolymer 4 (80 wt %) + PP (20 wt %) | Block Copolymer 4 (90 wt %) + PP (10 wt %) | Block Copolymer 4 (60 wt %) + PP (40 wt %) | Block Copolymer 4 (80 wt %) + PP (20 wt %) | Block Copolymer 4 (80 wt %) + PP (20 wt %) | None |
| Layer (III) (Outer Layer) | Block Copolymer 1 | Block Copolymer 2 | None | Block Copolymer 1 | None | None |
| Irradiation Dose (kGy) | 300 | 400 | 200 | 0 | 300 | 300 |
| Abrasion Resistance |  |  |  |  |  |  |
| Inner Surface | ○ | ○ | ○ | X | X | Not Testable |
| Outer Surface | ○ | ○ | X | X | X |  |
| Elastic Modulus (MPa) |  |  |  |  |  |  |
| Surface Layer (I) | — | — | — | — | — | 140 |
| Layer (II) | 9.7 | 4.8 | 51.5 | 9.7 | 9.7 | — |
| Transparency |  |  |  |  |  |  |
| Evaluation | ○ | ○ | ○ | ○ | ○ | ○ |
| Antifouling Property |  |  |  |  |  |  |
| Inner Surface | ○ | ○ | ○ | X | X | ○ |
| Outer Surface | ○ | ○ | X | X | X | ○ |
| Blood Compatibility |  |  |  |  |  |  |
| Hemolysis Ratio (%) by Surface Layer (I) | 0.1 | 0.2 | 0.2 | 1.0 | 0.1 | 0.2 |
| Evaluation | ○ | ○ | ○ | ○ | ○ | ○ |

*PP: Polypropylene
PE: Polyethylene

Chemical Co., Ltd.], stearic acid, calcium stearate, and oleylamide. Multilayer tubes were produced at a setting of 170° to 200° C. with a coextrusion multilayer tube molding machine in accordance with Table 4. Each of the thicknesses of the surface layer (I) (inner layer) and the layer (III) (outer layer) was set at 0.1 mm, an outer diameter was set at 12 mm, and an inner diameter was set at 8 mm. The resulting tubes were placed in a polyamide bag charged with nitrogen, and the bag was sealed. Cross-linking was applied to each of the tubes by the irradiation with an electron beam at acceleration energy of 4.6 MeV, and an irradiation dose under the conditions as shown in Table 4. The abrasion resistance and the transparency of these tubes were evaluated. In addition, the elastic modulus of a resin layer constituting the layer (II) was also determined. The results are shown in Table 4.

sheet was placed in a polyamide bag charged with nitrogen, and the bag was sealed. Cross-linking was applied to the sheet by the irradiation with an electron beam at acceleration energy of 4.6 MeV and an irradiation dose of 300 kGy. This sheet [corresponding to the surface layer (I) of the laminate of the present invention] is adopted as a sheet of Preparation Example 5. Meanwhile, a sheet which was not irradiated with an electron beam is adopted as a sheet of Preparation Example 6. The heat resistance was evaluated for these sheets. The results are shown in FIG. 2.

Figure 2:
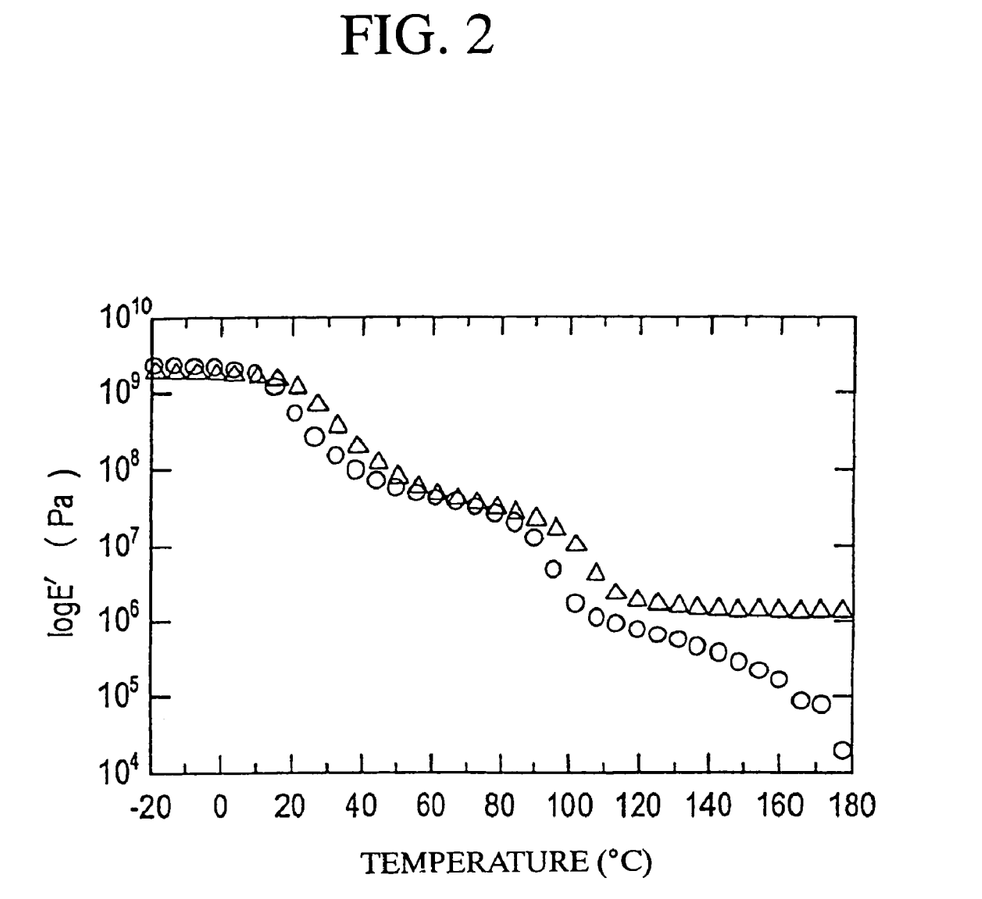
FIG. 2 is a graph of the storage modulus against the temperature of the sheet. In the figure, open triangles show the results of the sheet of the Preparation Example 5, and open circles show the results of the sheet of Preparation Example 6.

The results of the determined storage moduli of each of the sheets with respect to the temperature are shown in FIG. 2. At 120° C. or higher, the sheet of Preparation Example 5 was not found to have a lowered storage modulus, so that it is considered that the sheet can sufficiently withstand high-

TABLE 4

| | Comp. Ex. 7 | Comp. Ex. 8 | Comp. Ex. 9 | Comp. Ex. 10 | Comp. Ex. 11 | Comp. Ex. 12 |
|---|---|---|---|---|---|---|
| Surface Layer (I) (Inner Layer) | Low-Density PE | Low-Density PE (100 parts by wt.) + Silane-Grafted PE (2 parts by wt.) | Low-Density PE (100 parts by wt.) + Silicone Oil (2 parts by wt.) | Low-Density PE (100 parts by wt.) + Stearic Acid (2 parts by wt.) | Low-Density PE (100 parts by wt.) + Oleyl-amide (2 parts by wt.) | EVA (100 parts by wt.) + Calcium Stearate (2 parts by wt.) |
| Layer (II) (Intermediate Layer) | 12-Nylon | Polyamide Elastomer | Polybutylene Terephthalate | Aromatic Polyester-Aliphatic Polyester Copolymer | Aromatic Polyester-Aliphatic Polyester Copolymer | Aromatic Polyester-Aliphatic Polyester Copolymer |
| Layer (III) (Outer Layer) | Low-Density PE | Low-Density PE (100 parts by wt.) + Silane-Grafted PE (2 parts by wt.) | Low-Density PE (100 parts by wt.) + Silicone Oil (2 parts by wt.) | Low-Density PE (100 parts by wt.) + Stearic Acid (2 parts by wt.) | Low-Density PE (100 parts by wt.) + Oleyl-amide (2 parts by wt.) | EVA (100 parts by wt.) + Calcium Stearate (2 parts by wt.) |
| Irradiation Dose (kGy) | 100 | 100 | 100 | 100 | 100 | 100 |
| Abrasion Resistance | | | | | | |
| Inner Surface | Not Testable | Not Testable | Not Testable | Not Testable | Not Testable | Not Testable |
| Outer Surface | Not Testable | Not Testable | Not Testable | Not Testable | Not Testable | Not Testable |
| Elastic Modulus (MPa) | | | | | | |
| Layer (II) | 1600 | 340 | 8800 | 190 | 190 | 190 |
| Transparency | | | | | | |
| Evaluation | X | X | X | X | X | X |

*PE: Polyethylene
EVA: Ethylene-vinyl acetate copolymer

From Table 4, in the multilayer tubes of Comparative Examples 7 to 12, the layer (II) (intermediate layer) occupying a majority of the tube was rigid (high value of elastic modulus), so that a blood pump did not operate normally. In addition, air bubbles in the tube could not be recognized clearly.

Reference Test Example

A sheet having a thickness of 1 mm was produced at a setting of 170° C. using the block copolymer 1 obtained in Preparation Example 1, with a heat-pressing machine (manufactured by Shinto Kinzoku Kogyosho). The resulting pressure steam sterilization (for instance, conditions of 121° C., 205 Pa, 20 minutes). Contrary, the sheet of Preparation Example 6 was found to have a lowered storage modulus, so that it is considered that the sheet is easily deformed during the high-pressure steam sterilization.

Example 7

A blood bag (dimensions: 15 cm×10 cm, thickness: 1 mm) was produced using the sheet produced in Example 3. This blood bag was excellent in transparency, antifouling property and blood compatibility, thereby making it suitable for a blood bag.

Example 8

A pump tube of a blood circuit was produced using the three-layered tube produced in Example 4. When this pump tube was mounted on a blood pump to circulate distilled water, a pumping rate was stable. The pump tube exhibited abrasion resistance and transparency of the same levels as those of the currently used polyvinyl chloride pump tube. In addition, since this tube does not contain a plasticizer or a softening agent, these components would not be eluted into blood, thereby making it preferable as a blood circuit (medical device).

Example 9

A three-layered tube was produced at a setting 170° to 200° C. with a coextrusion multilayer tube molding machine (manufactured by Ikegai Corporation) in accordance with Table 5 using the block copolymer 1 obtained in Preparation Example 1, the block copolymer 4 obtained in Preparation Example 4, and a random type polypropylene [J215W (trade name), manufactured by Grand Polymer Co., Ltd.]. Each of the thicknesses of the surface layer (I) (inner layer) and the layer (III) (outer layer) was set at 0.1 mm, an outer diameter was set at 12 mm, and an inner diameter was set at 8 mm. The resulting tube was placed in a polyamide bag charged with nitrogen, and the bag was sealed. Cross-linking was applied to the tube by the irradiation with an electron beam at acceleration energy of 4.6 MeV and an irradiation dose of 60 kGy. The abrasion resistance, the transparency, the antifouling property and the blood compatibility of this tube were evaluated. In addition, the elastic modulus of a resin layer constituting the layer (II) was also determined. The results are shown in Table 5. It can be seen from Table 5 that the resulting three-layered tube is excellent in abrasion resistance, transparency, antifouling property and blood compatibility.

In addition, the same procedures as those for the above-mentioned evaluation of the abrasion resistance were carried out using the above three-layered tube, except that the tube was covered so that a dust in the air does not enter thereinto, and that a 4-hour operation was changed to a 24-hour operation. As a result, the damages were not observed on the inner surface of the tube. Entire circulated water was filtered through a membrane filter having a pore diameter of 0.8 μm, and the number of particles of 20 μm or larger on the membrane filter was counted to be 32. The number of particles of 20 μm or larger contained in the same volume of water before the test was determined to be 20 in accordance with the above determination method. Therefore, there was little detachment from the inner surface of the tube caused by friction with a blood pump for 24 hours, thereby showing an excellent abrasion resistance. Further, since the layer (II) (intermediate layer) occupying a majority of the tube was flexible (low value of elastic modulus), the blood pump operated normally.

TABLE 5

|  | Ex. 9 |
|---|---|
| Surface Layer (I) (Inner Layer) | Block Copolymer 1 |
| Layer (II) (Intermediate Layer) | Block Copolymer 4 (80 wt %) + PP(20 wt %) |
| Layer (III) | Block |

TABLE 5-continued

|  | Ex. 9 |
|---|---|
| (Outer Layer) | Copolymer 4 (50 wt %) + PP(50 wt %) |
| Irradiation Dose (kGy) | 60 |
| Abrasion Resistance |  |
| Inner Surface | ◯ |
| Outer Surface | ◯ |
| Elastic Modulus (MPa) |  |
| Layer (II) | 9.7 |
| Transparency |  |
| Evaluation | ◯ |
| Antifouling Property |  |
| Inner Surface | ◯ |
| Outer Surface | ◯ |
| Blood Compatibility |  |
| Hemolysis Ratio (%) by Surface Layer (I) | 0.1 |
| Evaluation | ◯ |

*PP: Polypropylene

INDUSTRIAL APPLICABILITY

According to the present invention, there is provided a laminate used in industries, foods and medicine, wherein the laminate has satisfactory abrasion resistance and flexibility, is excellent in transparency, antifouling property, heat resistance and blood compatibility, and is free from any problems in safety. The laminate is especially suitable for applications such as a precise experimental tube, a food tube, and a medical tube for a blood circuit or the like.

The invention claimed is:

1. A laminate comprising at least a surface layer (I) and an adjacent layer (II) thereto, wherein the surface layer (I) comprises a cross-linked copolymer formed by cross-linking a copolymer prepared by using as monomers at least one vinyl aromatic compound and at least one conjugated diene compound, and the adjacent layer (II) comprises a hydrogenated copolymer formed by hydrogenating a copolymer prepared by using as monomers at least one vinyl aromatic compound and at least one conjugated diene compound, wherein the copolymer in the surface layer (I) and/or the adjacent layer (II) is a block copolymer; the conjugated diene compound used in the preparation of the copolymer in the surface layer (I) and/or the adjacent layer (II) includes isoprene and/or butadiene; the vinyl aromatic compound used in the preparation of the copolymer in the surface layer (I) and/or the adjacent layer (II) includes styrene; and the content of the vinyl aromatic compound in the copolymer in the surface layer (I) and/or the adjacent layer (II) is from 10 to 40% by weight.

2. The laminate according to claim 1, wherein the surface layer (I) does not contain a plasticizer, a softening agent or an extender.

3. The laminate according to claim 1, wherein the surface layer (I) does not contain a cross-linking agent or a cross-linking aid.

4. The laminate according to claim 1, wherein the cross-linking is carried out by irradiation with active energy beams.

5. The laminate according to claim 4, wherein the active energy beam is electron beam.

6. The laminate according to claim 1, wherein the laminate has two surface layers, and one of the surface layers or both of the surface layers are the surface layer (I).

7. The laminate according to claim 1, wherein the hydrogenation ratio of the hydrogenated copolymer is 80% or more.

8. The laminate according to claim 1, wherein the adjacent layer (II) comprises 60 to 100% by weight of the hydrogenated copolymer and 0 to 40% by weight of a polyolefin resin.

9. A multilayer tube comprising the laminate of any one of claims 1 and 2 to 8.

10. A medical device comprising the multilayer tube of claim 9.

11. A medical device comprising the laminate of any one of claims 1 and 2 to 8.

12. The laminate according to claim 1, which is transparent.

* * * * *